United States Patent [19]

Oharu et al.

[11] Patent Number: 5,648,568
[45] Date of Patent: Jul. 15, 1997

[54] METHOD FOR PRODUCING A HYDROFLUOROCARBON

[75] Inventors: Kazuya Oharu; Ryuji Seki; Seisaku Kumai, all of Yokohama, Japan

[73] Assignee: Asahi Glass Company Ltd., Tokyo, Japan

[21] Appl. No.: 460,871

[22] Filed: Jun. 5, 1995

Related U.S. Application Data

[63] Continuation-in-part of Ser. No. 411,843, Mar. 28, 1995, which is a continuation of Ser. No. 266,471, Jun. 27, 1994, abandoned.

[30] Foreign Application Priority Data

| Jun. 30, 1993 | [JP] | Japan | 5-187261 |
| Jul. 9, 1993 | [JP] | Japan | 5-194200 |
| Dec. 14, 1993 | [JP] | Japan | 5-313243 |
| Mar. 22, 1994 | [JP] | Japan | 6-50816 |

[51] Int. Cl.$^6$ .................................................. C07C 19/08
[52] U.S. Cl. .................................................. 570/176
[58] Field of Search .................................................. 570/177

[56] References Cited

U.S. PATENT DOCUMENTS 3,042,727  7/1962  Olslowski et al. .................. 570/176

*Primary Examiner*—Alan Siegel
*Attorney, Agent, or Firm*—Oblon, Spivak, mcClelland, Maier & Neustadt, P.C.

[57] ABSTRACT

A method for producing a hydrofluorocarbon of the formula $H_nR_fH$ wherein n is 0 or 1, and when n is 0, $R_f$ is a $C_{2-12}$ linear or branched polyfluoroalkyl group, and when n is 1, $R_f$ is a $C_{2-12}$ linear or branched polyfluoroalkylene group, which comprises reacting an iodofluorocarbon of the formula $I_nR_fI$ wherein n and $R_f$ are as defined above, with hydrogen at a temperature of not higher than 450° C. in a gas phase.

18 Claims, No Drawings

METHOD FOR PRODUCING A HYDROFLUOROCARBON

This application is a continuation-in-part of U.S. patent application Ser. No. 08/411,843 filed Mar. 28, 1995 (which is a continuation of U.S. patent application Ser. No. 08/266,471 filed Jun. 27, 1994, now abandoned and incorporated entirely herein by reference.

The present invention relates to a novel method for producing a hydrofluorocarbon.

The following reports have been made with respect to methods for preparing a hydrofluorocarbon using an iodofluorocarbon as a starting material.

A method of conducting the reduction in the presence of the zinc (J. Fluorine Chem., 6,297, 1975). A method for the synthesis by a reaction employing a Grignard reagent (J. Fluorine Chem., 3,247, 1973). A method for the synthesis by a liquid phase reduction reaction employing hydrogen and a Raney nickel catalyst (Ger. Offen. 2,060,041, J. Chem. Soc., 3761,1953). A method for the synthesis by a reduction reaction by employing sodium hypophosphite and a palladium or platinum catalyst (J. Fluorine Chem., 55,101, 1991). A method of reacting a starting material with alcoholic KOH (J. Chem. Soc., 3761, 1953). A method of reacting the starting material with an alkali metal hydroxide in methanol (EP 0,449,516 A1).

However, the above conventional methods were all liquid phase reactions, and they were batch reactions. Therefore, they were poor in the productivity and had a problem such that the large amount of an inflammable organic solvent was required or high pressure hydrogen was required for the reaction.

The present inventors have conducted extensive studies on a method for efficiently producing a hydrofluorocarbon using an iodofluorocarbon as a starting material and as a result, have found a method whereby a hydrofluorocarbon can be obtained continuously at a high selectivity in good yield by reacting the iodofluorocarbon in a gas phase.

Thus, the present invention provides a method for producing a hydrofluorocarbon of the formula $H_nR_fH$ wherein n is 0 or 1, and when n is 0, $R_f$ is a $C_{2-12}$ linear or branched polyfluoroalkyl group, and when n is 1, $R_f$ is a $C_{2-12}$ linear or branched polyfluoroalkylene group, which comprises reacting an iodofluorocarbon of the formula $I_nR_fI$ wherein n and $R_f$ are as defined above, with a reducing agent in a gas phase.

Now, the present invention will be described in detail with reference to the preferred embodiments.

The iodofluorocarbon used as a starting material of the present invention is a compound of the formula $I_nR_fI$, wherein n is 0 or 1, and when n is 0, $R_f$ is a $C_{2-12}$ linear or branched polyfluoroalkyl group, preferably a $C_{3-8}$ polyfluoroalkyl group, and when n is 1, $R_f$ is a $C_{2-12}$ linear or branched polyfluoroalkylene group, preferably a $C_{3-8}$ polyfluoroalkylene group.

$R_f$ is preferably a polyfluoroalkyl group or polyfluoroalkylene group wherein (number of fluorine atoms)/(number of fluorine atoms+number of hydrogen atoms) is from 80 to 100%. Particularly preferred is a perfluoroalkyl group or a perfluoroalkylene group. When $R_f$ is a perfluoroalkyl group, its carbon number is preferably from 4 to 10, and when $R_f$ is a perfluoroalkylene group, its carbon number is preferably from 4 to 8. Further, $R_f$ preferably has a linear structure. As a linear perfluoroalkyl group, $CF_3CF_2CF_2CF_2CF_2CF_2$— is preferred. As a linear perfluoroalkylene group, $-CF_2CF_2CF_2CF_2$— is preferred.

Specific examples of the iodofluorocarbon include 1-iodo-1,1,2,2,2-pentafluoroethane $ICF_2CF_3$, 1-iodo-1,1,2,2,3,3,4,4,4-nonafluorobutane $I(CF_2)_4F$, 1-iodo-1,1,2,2,3,3,4,4,5,5,6,6,6-tridecafluorohexane $I(CF_2)_6F$, 1-iodo-1,1,2,2,3,3,4,4,5,5,6,6,7,7,8,8,8-heptadecafluorooctane $I(CF_2)_8F$, 2-iodo-1,1,1,2,3,3,3-heptafluoropropane $CF_3CFICF_3$, 4-iodo-1,1,1,2,3,3,4,4-octafluoro-2-trifluoromethylbutane $(CF_3)_2CF(CF_2)_2I$, 6-iodo-1,1,1,2,3,3,4,4,5,5,6,6-dodecafluoro-2-trifluoromethylhexane $(CF_3)_2CF(CF_2)_4I$, 1,2-diiodo-1,1,2,2-tetrafluoroethane $I(CF_2)_2I$, 1,4-diiodo-1,1,2,2,3,3,4,4-octafluorobutane $I(CF_2)_4I$, and 1,6-diiodo-1,1,2,2,3,3,4,4,5,5,6,6-dodecafluorohexane $I(CF_2)_6I$. However, the iodofluorocarbon is not limited to such specific examples.

It is the feature of the present invention to react the above iodofluorocarbon in a gas phase under an action of a reducing agent. The reducing agent is not particularly limited so long as it can be a hydrogen source in the reaction of the present invention, and hydrogen or an organic compound having hydrogen atoms bonded to a carbon atom, is preferred. Particularly preferred is an organic compound having hydrogen atoms bonded to a carbon atom. The organic compound preferably has a carbon number of at most 8, more preferably at most 4. Further, the organic compound is preferably a hydrocarbon or an organic compound containing an oxygen atom. The organic compound containing an oxygen atom is preferably an organic compound having at least one group selected from the group consisting of a hydroxyl group, a carboxyl group, an ether group, a carbonyl group, a carbonyloxy group and a formyl group. Further, preferred as the organic compound is at least one organic compound selected from the group consisting of alcohols, carboxylic acids, carboxylic acid derivatives, aldehydes, glycols, ethers, and hydrocarbons.

In the present invention, the alcohols mean compounds having a monovalent hydrocarbon group and a hydroxyl group. The monovalent hydrocarbon group is preferably an alkyl group or an aryl group, more preferably an alkyl group. The carbon number of the alkyl group is preferably from 1 to 10, more preferably from 1 to 6, most preferably from 1 to 3. The hydroxyl group of the alcohols is preferably a primary hydroxyl group or a secondary hydroxyl group, more preferably a primary hydroxyl group. As the alcohols in the present invention, primary alcohols having the above alkyl group and a primary hydroxyl group, or a secondary alcohols having the above alkyl group and a secondary hydroxyl group, are preferred. Particularly preferred are primary alcohols, since they are excellent in selectivity.

The primary alcohols include, for example, methanol, ethanol, 1-propanol, 1-butanol and 2-methyl-1-propanol. Particularly preferred is methanol or ethanol, since it is excellent in the reactivity and the productivity. As secondary alcohols, 2-propanol and 2-butanol are, for example, preferred.

As alcohols, both a primary alcohol and a secondary alcohol may be employed. In such a case, the proportions of the primary alcohol and the secondary alcohol are not particularly limited, and any optional proportions may be employed.

The carboxylic acids in the present invention are meant for an aromatic compound or an aliphatic compound having at least one carboxyl group, preferably only one carboxyl group. The carboxylic acids are preferably formic acid, acetic acid, propionic acid, malonic acid and succinic acid. Particularly preferred is formic acid, since it produces little by-products.

The carboxylic acid derivatives in the present invention are meant for compounds obtainable by a dehydration reaction of the carboxyl groups of the above carboxylic acids with other compounds. For example, they include carboxylic acid esters and carboxylic acid amides. Carboxylic acid esters are preferred.

As the carboxylic acid esters, alkyl esters of the above-mentioned carboxylic acids are preferred. Particularly preferred are methyl formate, ethyl formate, butyl formate, pentyl formate, methyl acetate, ethyl acetate, isobutyl acetate, isopropyl acetate, methyl propionate, methyl malonate, diethyl malonate, diethyl phthalate, and di-2-ethylhexyl phthalate. Especially preferred is methyl acetate, since it produces little by-products. As the carboxylic acid amides, the formic acid amide, acetic acid amide, N,N-dimethylformamide and N,N-dimethylacetamide are, for example, preferred.

The aldehydes in the present invention are meant for compounds having a formyl group. As such aldehydes, formaldehyde and acetaldehyde are, for example, preferred.

The ethers in the present invention are meant for compounds containing at least one structure wherein two hydrocarbon groups are bonded to one oxygen atom. As such hydrocarbon groups, aliphatic hydrocarbon groups are preferred. The carbon number of such hydrocarbon groups are preferably from 1 to 6, more preferably from 1 to 4. As such ethers, diethyl ether, tetrahydrofuran, and 1,4-dioxane are, for example, preferred.

The glycols in the present invention are meant for aliphatic compounds wherein two hydroxyl groups are bonded to two different hydrocarbon groups or compounds wherein hydrogens of such two hydroxyl groups are substituted by hydrocarbon groups. As such glycols, ethylene glycol, diethylene glycol, propylene glycol, dipropylene glycol, ethylene glycol dimethyl ether (glyme), diethylene glycol dimethyl ether (diglyme) and propylene glycol dimethyl ether are, for example, preferred.

The ketones in the present invention are meant for compounds wherein a carbonyl group is bonded to two carbon atoms. As such ketones, acetone, methyl ethyl ketone, methyl isobutyl ketone and acetylacetone are, for example, preferred.

The hydrocarbons are meant for aliphatic hydrocarbons and aromatic hydrocarbons. As the aliphatic hydrocarbons, saturated hydrocarbons having from 1 to 6 carbon atoms are preferred, and particularly preferred are, for example, methane, ethane, propane and butane. As the aromatic hydrocarbons, compounds containing a benzene ring are preferred, and particularly preferred are compounds wherein substituents are bonded to the benzene ring. Toluene and xylene are, for example, preferred.

Among the above reducing agents, alcohols and carboxylic acids are particularly preferred as the reducing agent in the present invention from the viewpoint of handling efficiently, reactivity and economy. Particularly preferred are alcohols.

The proportions of the starting material iodofluorocarbon and the above reducing agent may be varied to a large extent. Usually a stoichiometric amount of the reducing agent is used to reduce the iodine atoms. However, to let the starting material iodofluorocarbon react substantially completely, the reducing agent may be used in a substantially larger amount than the stoichiometric amount, namely, twice or more in an equivalent amount to the total equivalent of the iodine atoms in the iodofluorocarbon. In a usual case, the reducing agent is used in an amount of from 1 to 5 times in an equivalent amount to one equivalent of iodine atoms in the starting material iodofluorocarbon. If the amount of the reducing agent is small, not only the conversion in the reaction tends to be low, but also production of a dimer of the formula $R_f$—$R_f$ wherein $R_f$ is a $C_{2-12}$ linear or branched polyfluoroalkyl group, as a by-product, will increase, such being undesirable.

Further, when the reducing agent is hydrogen, it is preferred that a hydrogenation catalyst is present in the reaction of the present invention. On the other hand, when the reducing agent is the above-mentioned organic compound, the reaction may be conducted either in the presence of a hydrogenation catalyst or in the absence of a catalyst. However, it is rather preferred to conduct the reaction in the absence of a catalyst, when preparation of the catalyst, complexity of the structure of the reactor, post treatment of the waste catalyst, etc. are taken into consideration.

When a hydrogenation catalyst is used for the reaction of the present invention, the efficiency of the reaction can be increased. The hydrogenation catalyst is not particularly limited and may be selected for use from conventional hydrogenation catalysts. In the present invention, it is preferred to use, among such conventional catalysts, alumina, active carbon, zeolite or a hydrogenation catalyst containing at least one element selected from the group consisting of Group 8 elements. It is particularly preferred to use a catalyst containing at least one element selected from the group consisting of Group 8 elements. The Group 8 elements include palladium, ruthenium, rhodium, platinum, nickel, cobalt and iridium. In the present invention, the catalyst preferably contains, among such elements, a platinum group element such as ruthenium, rhodium, palladium or platinum from the viewpoint of the durability of the catalyst. Particularly preferred is a catalyst containing palladium. Especially preferred is a catalyst having gold or silver mixed or alloyed to palladium, since not only the durability of the catalyst but also the reactivity will be thereby increased.

Further, as a hydrogenation catalyst of the present invention, a hydrogenation catalyst having at least one member selected from the above-mentioned Group 8 elements supported on a carrier, is preferred. The carrier is not particularly limited and may be selected for use from carriers which are commonly used as carriers for catalysts. For example, alumina, active carbon, silica-alumina such as zeolite, or zirconia is preferred. Particularly preferred is active carbon, since it is readily available. As the hydrogenation catalyst, active carbon having palladium supported thereon, active carbon having an alloy of palladium and gold supported thereon, or active carbon having platinum supported thereon, is, for example, preferred. The amount of the Group 8 element supported is not particularly limited, but it is preferred to have it supported in an amount of from 0.01 to 20 wt %, more preferably from 1 to 5 wt %, in the catalyst. The manner for supporting the Group 8 element on the above catalyst is not particularly limited, and a conventional method for preparation of a novel catalyst can be used. Further, it is preferred to apply reducing treatment after the preparation of the catalyst, so that stabilized properties can thereby obtained.

The reaction of the present invention can be conducted in the presence of an inert gas. The inert gas may be nitrogen or a rare gas. The rare gas is, for example, preferably argon, helium or neon. Among them, nitrogen or helium is preferred as the inert gas from the viewpoint of availability and handling efficiency. The amount of the inert gas to be present is not particularly limited. However, if the amount is too much, the yield may decrease. Therefore, in a usual case, such an inert gas is introduced in an amount of not more than about 50 vol % in a gas phase of the above iodofluorocarbon and hydrogen or a hydrogen-containing organic compound.

In the gas phase reaction, the reaction temperature varies depending on the presence or absence of a catalyst.

When an organic compound is used as a reducing agent, there is a fear of by-producing a tar-like material derived from the organic compound if the reaction is conducted at such a temperature as exceeding 500° C., and it is therefore preferable to conduct the reaction at a temperature in the range of from 180° to 500° C. Particularly, the reaction temperature is preferably from 300° to 480° C. in the absence of a catalyst, and is preferably from 180° to 320° C. in the presence of a catalyst in order to prevent the catalyst activity from being lowered by a tar-like material by-produced.

When hydrogen is used as a reducing agent, there is a fear of decomposing a starting material to produce a by-product if the reaction is conducted at such a temperature as exceeding 500° C., and it is therefore preferable to conduct the reaction at a temperature in the range of from 150° to 450° C. Particularly, the reaction temperature is preferably from 300° to 450° C. in the absence of a catalyst, and is preferably from 200° to 350° C. in the presence of a catalyst. In either case, the conversion tends to be low as the reaction temperature decreases. The reaction time is usually preferably from 0.1 to 300 seconds, more preferably from 2 to 60 seconds. If the reaction time is too short, the conversion tends to be low. On the other hand, if the reaction time is too long, formation of by-products tends to increase. With respect to the reaction pressure in a case where the reaction is conducted by means of hydrogen, the pressure is usually from 0 to 10 atm, preferably from 0 to 3 atm, as gauge pressure, from the viewpoint of safety. When a reducing agent other than hydrogen is employed, the pressure is not particularly limited, and atmospheric pressure, reduced pressure or elevated pressure may be employed. However, usually, the pressure is at a level of from 0.5 to 5 atm as gauge pressure.

The hydrofluorocarbon to be formed by the above reaction is a compound of the formula $H_nR_fH$. In this formula, n is 0 or 1. When n is 0, $R_f$ is a $C_{2-12}$ linear or branched polyfluoroalkyl group, preferably a $C_{3-8}$ polyfluoroalkyl group, particularly preferably $CF_3CF_2CF_2CF_2CF_2CF_2$—. When n is 1, $R_f$ is a $C_{2-12}$ linear or branched polyfluoroalkylene group, preferably a $C_{3-8}$ polyfluoroalkylene group, particularly preferably —$CF_2CF_2CF_2CF_2$—.

Specific examples of the hydrofluorocarbon include 1,1,1,2,2-pentafluoroethane $F(CF_2)_2H$, 1,1,1,2,2,3,3,4,4-nonafluorobutane $F(CF_2)_4H$, 1,1,1,2,2,3,3,4,4,5,5,6,6-tridecafluorohexane $F(CF_2)_6H$, 1,1,1,2,2,3,3,4,4,5,5,6,6,7,7,8,8-heptadecafluorooctane $F(CF_2)_8H$, 1,1,1,2,3,3,3-heptafluoropropane $CF_3CFHCF_3$, 1,1,1,2,3,3,4,4-octafluoro-2-trifluoromethylbutane $(CF_3)_2CF(CF_2)_2H$, 1,1,1,2,3,3,4,4,5,5,6,6-dodecafluoro-2-trifluoromethylhexane $(CF_3)_2CF(CF_2)_4H$, 1,1,2,2-tetrafluoroethane $H(CF_2)_2H$, 1,1,2,2,3,3,4,4-octafluorobutane $H(CF_2)_4H$ and 1,1,2,2,3,3,4,4,5,5,6,6-dodecafluorohexane $H(CF_2)_6H$.

The above reaction of the present invention is an excellent reaction showing a high degree of conversion. The obtained crude reaction solution of a hydrofluorocarbon is usually passed through an aqueous alkaline solution to remove e.g. a formed inorganic iodine compound and to obtain a product. As such an aqueous alkaline solution, an aqueous solution of an alkali metal hydroxide is preferred, and sodium hydroxide or potassium hydroxide is preferred. In a usual case, the concentration of the aqueous solution of an alkali metal hydroxide is preferably from 5 to 50 wt %, more preferably from 10 to 30 wt %. When it is desired to obtain a product of a higher purity, the product may further be subjected to purification by distillation.

In a case where no adequate purification can be attained by distillation or in a case where it is desired to obtain a hydrofluorocarbon of a much higher purity, the crude reaction solution or the reaction product having passed through an aqueous solution of an alkali metal hydroxide in accordance with the above described method, is preferably treated with an alkali metal hydroxide. By the treatment with the alkali metal hydroxide, impurities contained in the hydrofluorocarbon, particularly various organic iodine compounds derived from the iodofluorocarbon, can efficiently be removed. As such an alkali metal hydroxide, potassium hydroxide or sodium hydroxide is, for example, preferred. The amount of the alkali metal hydroxide is preferably in an large excess amount relative to the amount of impurities, and it is usually preferably at least about 10 mols per mol of the impurities.

The treatment with the alkali metal hydroxide is usually preferably conducted under heating in the presence of an organic solvent. The organic solvent is not particularly limited, and known or well known organic solvents may be employed. As such organic solvents, alcohols, ethers and ketones are, for example, preferred. Particularly preferred are alcohols in view of the high reactivity and the solubility of the alkali metal hydroxide.

The alcohols, ethers and ketones may, for example, be the same compounds as mentioned above with respect to the reducing agent. However, as the alcohols for the purification step, methanol, ethanol, propanol, butanol, isopropanol and isobutanol are, for example, preferred and particularly preferred is methanol or ethanol. As the ethers, diethyl ether, tetrahydrofuran, 1,4-dioxane and ethylene glycol dimethyl ether are, for example, preferred. As the ketones, acetone, methyl ethyl ketone, methyl isobutyl ketone and acetyl ketone are, for example, preferred.

As the organic solvent, one or more of the above organic solvents may be employed. The amount of the organic solvent is not particularly limited, and it is preferably an amount whereby the above alkali metal hydroxide can be dissolved.

The treating temperature is usually preferably from 0° to 200° C. In a case where an organic solvent is employed, the temperature is preferably at a refluxing temperature of the solvent. The temperature may vary depending upon the presence or absence, or the type of the organic solvent. The pressure may be reduced pressure, atmospheric pressure or elevated pressure. However, it is usually atmospheric pressure. The treating time is usually from 0.1 to 10 hours, preferably from 0.1 to 2 hours.

In a usual case, the hydrofluorocarbon treated with an alkali metal hydroxide, is washed with water to remove formed alkali metal iodides and to obtain a product of a high purity. Further, if desired, it may further be purified by distillation to obtain a product of a higher purity.

The hydrofluorocarbon thus obtained is less influential over the environment as compared with conventional chlorinated hydrocarbons or chlorinated fluorohydrocarbons. Not only that, it is useful for similar applications, for example, for a blowing agent, a cooling medium or a cleaning agent. Further, the hydrofluorocarbon prepared by the method of the present invention has a low content of an unreacted iodofluorocarbon or other impurities, whereby adverse effects attributable to impurities can be avoided. Accordingly, when a polymerization reaction is carried out by using the hydrofluorocarbon obtained by the above method, as a solvent, the reaction can be conducted without coloring the polymer.

The polymer is not particularly limited, but particularly preferred is a fluorine-type polymer such as polytetrafluoroethylene, a copolymer of tetrafluoroethylene with perfluoroalkylvinyl ether or a copolymer of tetrafluoroethylene with ethylene.

Further, when a bromofluorocarbon or the like is prepared by using the hydrofluorocarbon prepared by the present invention as a starting material, and used as an artificial blood or as a contrast medium, there is a merit such that no coloring phenomenon attributable to iodine compounds will be observed.

Now, the present invention will be described in further detail with reference to Examples. However, it should be understood that the present invention is by no means restricted by such specific Examples.

EXAMPLES 1 TO 6

An Inconel 600 tubular reactor having an inner diameter of 2.54 cm and a length of 100 cm was heated in an electric furnace. As a starting material, $I(CF_2)_6F$ or $I(CF_2)_8F$ or $I(CF_2)_4I$ was vaporized by a preheater and introduced into the reactor under an atmospheric pressure together with hydrogen. At that time, the molar ratio of the hydrogen to the starting material was 2:1 (in Examples 1 to 4) or 4:1 (in Examples 5 and 6), the reaction temperature was 400° C. or 450° C., and the residence time in the reactor was 40 seconds. The reaction product was passed through a 20 wt % potassium hydroxide aqueous solution, then collected by a trap cooled to −78° C. The collected reaction product was analyzed by gas chromatography and NMR. The results are shown in Table 1.

TABLE 1

| | Starting material | Reaction temperature | Conversion (%) | Selectivity (%) |
|---|---|---|---|---|
| Example 1 | $I(CF_2)_6F$ | 400° C. | 85.6 | 96.2 |
| Example 2 | $I(CF_2)_6F$ | 450° C. | 92.6 | 93.2 |
| Example 3 | $I(CF_2)_8F$ | 400° C. | 80.2 | 95.1 |
| Example 4 | $I(CF_2)_8F$ | 450° C. | 90.3 | 89.6 |
| Example 5 | $I(CF_2)_4I$ | 400° C. | 82.3 | 94.9 |
| Example 6 | $I(CF_2)_4I$ | 450° C. | 90.5 | 91.0 |

EXAMPLE 7

An Inconel 600 U-shaped tubular reactor having an inner diameter of 2.54 cm and a length of 100 cm packed with 200 cc of palladium-supported active carbon (an amount of supported palladium: 2 wt %) was immersed in a salt bath furnace. A starting material $I(CF_2)_6F$ was vaporized by a preheater and introduced into the reactor under atmospheric pressure together with hydrogen. At that time, the molar ratio of the hydrogen to the starting material was 2:1, the reaction temperature was 250° C. and the contact time was 20 seconds. The reaction product was passed through a 20 wt % potassium hydroxide aqueous solution and then collected by a trap cooled to −78° C. The collected reaction product was analyzed by gas chromatography and NMR. The conversion of the starting material was 90.3%, and the selectivity for $H(CF_2)_6F$ was 98.3%.

EXAMPLES 8 TO 10

The reaction was carried out in the same manner as in Example 7 except that the reaction temperature was changed to 300° C., or as the catalyst, palladium-supported active carbon with the amount of supported palladium being 5 wt %, was used, or as the catalyst, a catalyst having 2 wt % of a Pd-Au alloy (Pd:Au=9:1 (weight ratio)) supported on active carbon, was used. The results are shown in Table 2.

TABLE 2

| | Catalyst | Reaction temperature | Conversion (%) | Selectivity (%) |
|---|---|---|---|---|
| Example 8 | Pd2%/C | 300° C. | 99.9 | 93.3 |
| Example 9 | Pd5%/C | 250° C. | 98.9 | 98.6 |
| Example 10 | PdAu2%/C | 250° C. | 99.9 | 99.3 |

EXAMPLES 11 AND 12

Using $I(CF_2)_8F$ as the starting material, the reaction was conducted in the same manner as in Example 7 (Example 11). Or the reaction was conducted in the same manner as in Example 11 except that the reaction temperature was changed to 300° C. (Example 12). The results are shown in Table 3.

TABLE 3

| | Starting material | Reaction temperature | Conversion (%) | Selectivity (%) |
|---|---|---|---|---|
| Example 11 | $I(CF_2)_8F$ | 250° C. | 88.6 | 96.1 |
| Example 12 | $I(CF_2)_8F$ | 300° C. | 99.2 | 91.2 |

EXAMPLE 13

The reaction was carried out in the same manner as in Example 7 except that as the starting material, $I(CF_2)_4I$ was used, as the catalyst, a catalyst having 2 wt % of a Pd-Au alloy (Pd:Au=9:1 (weight ratio)) supported on active carbon, was used, and the molar ratio of the hydrogen to the starting material was changed to 4:1. The conversion was 99.9%, and the selectivity was 98.4%.

EXAMPLES 14 TO 16

An Inconel 600 tubular reactor having an inner diameter of 2.54 cm and a length of 100 cm was heated in an electric furnace. A liquid having $I(CF_2)_6F$ and methanol mixed in a molar ratio of 1:5, was vaporized by a preheater and introduced into the reactor under atmospheric pressure. The reaction temperature was 350° C., 400° C. or 450° C., and the residence time in the reactor was 20 seconds. The reaction product was passed through a 20 wt % sodium hydroxide aqueous solution and then collected by a trap cooled to −78° C. The results are shown in Table 4.

TABLE 4

| | Reaction temperature | Conversion (%) | Selectivity (%) |
|---|---|---|---|
| Example 14 | 350° C. | 45.0 | 99.0 |
| Example 15 | 400° C. | 81.0 | 98.0 |
| Example 16 | 450° C. | 99.0 | 97.0 |

EXAMPLE 17

An Inconel 600 tubular reactor having an inner diameter of 2.54 cm and a length of 100 cm was heated in an electric furnace. A liquid having $I(CF_2)_6F$ and 2-propanol mixed in a molar ratio of 1:5, was vaporized by a preheater and introduced into the reactor under atmospheric pressure. The reaction temperature was 350° C., and the residence time in the reactor was 20 seconds. The reaction product was passed through a 20 wt % potassium hydroxide aqueous solution and then collected by a trap cooled to −78° C. The collected reaction product was analyzed, whereby the conversion was 98.1%, and the selectivity was 83.0%.

EXAMPLE 18

An Inconel 600 tubular reactor having an inner diameter of 2.54 cm and a length of 100 cm was heated in an electric furnace. A liquid having $I(CF_2)_4I$ and methanol mixed in a molar ratio of 1:5, was vaporized in a preheater and introduced into the reactor under atmospheric pressure. The reaction temperature was 350° C., and the residence time in the reactor was 20 seconds. The reaction product was passed through a 20 wt % potassium hydroxide aqueous solution and then collected by a trap cooled to −78° C. The collected reaction product was analyzed, whereby a monoiodo compound was contained in an amount of 18.3%. The conversion was 98.1%, and the selectivity was 78.6%.

EXAMPLES 19 TO 21

An Inconel 600 U-shaped tubular reactor having an inner diameter of 2.45 cm and a length of 100 cm, packed with 200 cc of palladium-supported active carbon (amount of supported palladium: 2 wt %) was immersed in a salt bath furnace. A liquid having $I(CF_2)_6F$ and methanol mixed in a molar ratio of 1:5, was vaporized by preheater and introduced into the reactor under atmospheric pressure. The reaction temperature was 200° C., 250° C. or 300° C., and the contact time was 20 seconds. The reaction product was passed through a 20 wt % potassium hydroxide aqueous solution and then collected by a trap cooled to −78° C. The results are shown in Table 5.

TABLE 5

| | Reaction temperature | Conversion (%) | Selectivity (%) |
|---|---|---|---|
| Example 19 | 200° C. | 93.0 | 99.0 |
| Example 20 | 250° C. | 98.0 | 99.0 |
| Example 21 | 300° C. | 100.0 | 92.0 |

EXAMPLE 22

The reaction was carried out in the same manner as in Example 19 except that the amount of supported palladium in the palladium-supported active carbon was changed to 5 wt %, and the reaction temperature was changed to 250° C. The conversion was 100.0%, and the selectivity was 98.0%.

EXAMPLES 23 AND 24

An Inconel 600 U-shaped tubular reactor having an inner diameter of 2.54 cm and a length of 100 cm, packed with 200 cc of palladium-supported active carbon (amount of supported palladium: 2 wt %) was immersed in a salt bath furnace. A liquid having $I(CF_2)_6F$ and a ethanol mixed in a molar ratio of 1:2, was vaporized in a preheater and introduced into the reactor under atmospheric pressure. The reaction temperature was 200° C. or 250° C., and the contact time was 20 seconds. The reaction product was passed through a 20 wt % potassium hydroxide aqueous solution and then collected by a trap cooled to −78° C. The results are shown in Table 6.

TABLE 6

| | Reaction temperature | Conversion (%) | Selectivity (%) |
|---|---|---|---|
| Example 23 | 200° C. | 99.4 | 98.4 |
| Example 24 | 250° C. | 100.0 | 97.0 |

EXAMPLE 25

An Inconel 600 tubular reactor having an inner diameter of 2.54 cm and a length of 100 cm was heated in an electric furnace. A liquid having $I(CF_2)_6F$, methanol and 2-propanol mixed in a molar ratio of 1:1:1, was vaporized in a preheater and introduced into the reactor under atmospheric pressure. The reaction temperature was 350° C., and the residence time in the reactor was 40 seconds. The reaction product was passed through a 20 wt % potassium hydroxide aqueous solution and then collected by a trap cooled to −78° C. The collected reaction product was analyzed, whereby the conversion was 81.4%, and the selectivity was 92.0%.

EXAMPLES 26 TO 29

An Inconel 600 tubular reactor having an inner diameter of 2.54 cm and a length of 100 cm was heated in an electric furnace. A liquid having $I(CF_2)_6F$ and ethanol mixed in a molar ratio of 1:2, was vaporized by a preheater, and nitrogen was introduced at a concentration of 20% (volume concentration) of the entire vaporized product, and the mixture was introduced into the reactor under atmospheric pressure. The reaction temperature was 335° C., 350° C., 370° C. or 400° C., and the residence time in the reactor was 40 seconds. The reaction product was passed through a 20 wt % potassium hydroxide aqueous solution and then collected by a trap cooled to −78° C. The collected reaction product was analyzed. The results are shown in Table 7.

TABLE 7

| | Reaction temperature | Conversion (%) | Selectivity (%) |
|---|---|---|---|
| Example 26 | 335° C. | 41.0 | 99.4 |
| Example 27 | 350° C. | 98.4 | 98.4 |
| Example 28 | 370° C. | 99.4 | 97.4 |
| Example 29 | 400° C. | 99.9 | 93.2 |

EXAMPLES 30 TO 33

An Inconel 600 tubular reactor having an inner diameter of 2.54 cm and a length of 100 cm was heated in an electric furnace. $I(CF_2)_6F$ and a formic acid in a molar ratio of 1:2.5 were, respectively, vaporized in a preheater and introduced into the reactor under atmospheric pressure. The reaction temperature was 360° C., 380° C., 400° C. or 420° C., and the residence time in the reactor was 30 seconds. The reaction product was passed through a 20 wt % potassium hydroxide aqueous solution and then collected by a trap cooled to −78° C. The collected reaction product was analyzed. The results are shown in Table 8.

TABLE 8

| | Reaction temperature | Conversion (%) | Selectivity (%) |
|---|---|---|---|
| Example 30 | 360° C. | 30.0 | 99.0 |
| Example 31 | 380° C. | 58.0 | 99.0 |
| Example 32 | 400° C. | 87.0 | 99.0 |

TABLE 8-continued

|  | Reaction temperature | Conversion (%) | Selectivity (%) |
|---|---|---|---|
| Example 33 | 420° C. | 99.0 | 99.0 |

EXAMPLE 34

An Inconel 600 tubular reactor having an inner diameter of 2.54 cm and a length of 100 cm was heated in an electric furnace. $I(CF_2)_4I$ and formic acid in a molar ratio of 1:2.5 were, respectively, vaporized in a preheater and introduced into the reactor under atmospheric pressure. The reaction temperature was 420° C., and the residence time in the reactor was 40 seconds. The reaction product was passed through a 20 wt % potassium hydroxide aqueous solution and then collected by a trap cooled to −78° C. The collected reaction product was analyzed, whereby a monoiodo compound was contained in an amount of 1.2%. The conversion was 99.5%, and the selectivity was 96.1%.

EXAMPLE 35

An Inconel 600 U-shaped tubular reactor having an inner diameter of 2.54 cm and a length of 100 cm, packed with 300 cc of granular active carbon (Granular Hakutaka active carbon, manufactured by Takeda Chemical Industry Company Ltd.) was immersed in a salt bath furnace. $I(CF_2)_6F$ and formic acid in a molar ratio of 1:1.5 were, respectively, vaporized in a preheater and introduced into a reactor under atmospheric pressure. The reaction temperature was 300° C., and the residence time in the reactor was 30 seconds. The reaction product was passed through a 20 wt % potassium hydroxide aqueous solution and then collected by a trap cooled to −78° C. The collected reaction product was analyzed, whereby the conversion was 100%, and the selectively was 97.7%.

EXAMPLES 36 TO 38

An Inconel 600 U-shaped tubular reactor having an inner diameter of 2.54 cm and a length of 100 cm, packed with 200 cc of palladium-supported active carbon (amount of supported palladium: 2 wt % or 5 wt %) was immersed in a salt bath furnace. $I(CF_2)_6F$ and formic acid in a molar ratio of 1:2.5 were, respectively, vaporized in a preheater and introduced into the reactor under atmospheric pressure. The reaction temperature was 200° C. or 250° C., and the contact time was 20 seconds. The reaction product was passed through a 20 wt % potassium hydroxide aqueous solution and then collected by a trap cooled to −78° C. The collected reaction product was analyzed. The results are shown in Table 9.

TABLE 9

|  | Catalyst | Reaction temperature | Conversion (%) | Selectivity (%) |
|---|---|---|---|---|
| Example 36 | Pd2%/C | 200° C. | 92.0 | 99.0 |
| Example 37 | Pd2%/C | 250° C. | 99.0 | 99.0 |
| Example 38 | Pd5%/C | 200° C. | 100.0 | 99.0 |

EXAMPLE 39

An Inconel 600 tubular reactor having an inner diameter of 2.54 cm and a length of 100 cm was heated in an electric furnace. $I(CF_2)_6F$ and formic acid in a molar ratio of 1:2.5 were, respectively, vaporized in a preheater, and nitrogen was introduced at a concentration of 20% (volume concentration) of the entire vaporized product. The mixture was introduced into the reactor under atmospheric pressure. The reaction temperature was 440° C., and the residence time in the reactor was 40 seconds. The reaction product was passed through a 20 wt % potassium hydroxide aqueous solution and then collected by a trap cooled to −78° C. The collected reaction product was analyzed, whereby the conversion was 99.9%, and the selectivity was 97.2%.

EXAMPLES 40 AND 41

An Inconel 600 tubular reactor having an inner diameter of 2.54 cm and a length of 100 cm was heated in an electric furnace. $I(CF_2)_6F$ and dioxane in a molar ratio of 1:2 were, respectively, vaporized in a preheater and introduced into the reactor under atmospheric pressure. The reaction temperature was 350° C. or 400° C., and the residence time in the reactor was 30 seconds. The reaction product was passed through a 20 wt % potassium hydroxide aqueous solution and then collected by a trap cooled to −78° C. The results are shown in Table 10.

TABLE 10

|  | Reaction temperature | Conversion (%) | Selectivity (%) |
|---|---|---|---|
| Example 40 | 350° C. | 84.0 | 91.0 |
| Example 41 | 400° C. | 100.0 | 95.0 |

EXAMPLES 42 TO 49

The reaction was carried out in the same manner as in Example 40 except that the reducing agent and the reaction temperature as identified in Table 11 were employed. The reducing agent employed, the reaction temperature and the results of analyses of the collected products are shown in Table 11.

TABLE 11

|  | Reducing agent | Reaction temperature | Conversion (%) | Selectivity (%) |
|---|---|---|---|---|
| Example 42 | glyme | 350° C. | 88 | 93 |
| Example 43 | glyme | 400° C. | 99 | 89 |
| Example 44 | acetone | 350° C. | 15 | 82 |
| Example 45 | acetone | 400° C. | 48 | 73 |
| Example 46 | toluene | 350° C. | 35 | 80 |
| Example 47 | toluene | 400° C. | 98 | 78 |
| Example 48 | ethyl acetate | 350° C. | 94 | 99 |
| Example 49 | ethyl acetate | 400° C. | 100 | 98 |

EXAMPLE 50

An Inconel 600 tubular reactor having an inner diameter of 2.54 cm and a length of 100 cm was heated in an electric furnace. A liquid having a starting material $I(CF_2)_6F$ and ethanol mixed in a molar ratio of 1:2, was vaporized by a preheater and introduced into the reactor under atmospheric pressure. The reaction temperature was 380° C., and the residence time in the reactor was 30 seconds. The reaction product was passed through a 20 wt % potassium hydroxide aqueous solution and then collected by a trap cooled to −78° C. The recovered crude reaction solution was analyzed by gas chromatography, whereby 88.5% of H(CF$_2$)$_6$F (boiling point: 71° C.), 5.7% of ethyl iodide (boiling point: 72° C.), 3.5% of ethyl acetate (boiling point: 77° C.), 1.3% of diethyl ether, 0.1% of an unreacted starting material and 0.9% of other impurities were contained.

EXAMPLES 51 TO 54

The reaction was carried out in the same manner as in Example 1, except that the starting materials and the reaction temperature as identified in Table 12 were employed. The molar ratio of hydrogen (used as a reducing agent) and the starting material was 2:1 in Examples 51 and 53, or 4:1 in Examples 52 and 54. The reaction temperature was 300° C. in Examples 51 and 52, or 350° C. in Examples 53 and 54, and the residence time in the tubular reactor was 40 seconds. The results are shown in Table 12.

TABLE 12

| Example | Starting material | Molar ratio of H$_2$/I(CF$_2$)$_6$F | Reaction temp. | Conversion (%) | Selectivity (%) |
|---|---|---|---|---|---|
| 51 | I(CF$_2$)$_6$F | 2/1 | 300° C. | 1.2 | 98.1 |
| 52 | I(CF$_2$)$_6$F | 4/1 | 300° C. | 3.4 | 97.8 |
| 53 | I(CF$_2$)$_6$F | 2/1 | 350° C. | 12.2 | 96.4 |
| 54 | I(CF$_2$)$_6$F | 4/1 | 350° C. | 56.3 | 97.2 |

COMPARATIVE EXAMPLES 1 TO 3

The reaction was carried out in the same manner as in Example 1, except that the starting materials and the reaction temperatures as identified in Table 13 were employed. The molar ratio of hydrogen (used as a reducing agent) and the starting material was 4:1, and the reaction temperature was 450° C. in Comparative Examples 1 and 2, or 550° C. in Comparative Example 3. The residence time in the tubular reactor was 40 seconds. The results are shown in Table 13.

TABLE 13

| Comparative Example | Starting material | Molar ratio of hydrogen/starting material | Reaction temp. | Conversion (%) | Selectivity (%) |
|---|---|---|---|---|---|
| 1 | CF$_3$Br | 4/1 | 450° C. | 3.1 | 98.8 |
| 2 | CF$_3$Cl | 4/1 | 450° C. | 0 | 0 |
| 3 | I(CF$_2$)$_6$F | 4/1 | 550° C. | 100 | 38.1 |

REFERENCE EXAMPLE 1

Into a 2 l four-necked flask equipped with a stirrer, a reflux condenser, a dropping funnel and a thermometer, 256 g of methanol, 30 g of 2-propanol and 74.3 g (1.13 mols) of 85% of potassium hydroxide were charged. The reactor was heated to an internal temperature of 60° C. Then, 1500 g of the crude reaction solution obtained in Example 50 was dropwise added over a period of one hour. After completion of the dropwise addition, refluxing was continued under heating for two hours. The reactor was cooled to room temperature, and then 300 g of water was added to dissolve precipitated potassium iodide. The crude reaction solution was separated into two layers. The fluorocarbon layer (lower layer) was further washed with 500 g of water. The fluorocarbon layer was analyzed, whereby the purity of C$_6$F$_{13}$H was 98.3%, ethyl iodide and ethyl acetate were not detected, and the amount of an unreacted starting material was not more than 10 ppm. Then, the obtained fluorocarbon layer was distilled by means of a distillation column with a theoretical plate number of 5 plates to obtain 1240 g of C$_6$F$_{13}$H having a purity of 99.995%. The obtained C$_6$F$_{13}$H was analyzed, whereby no unreacted starting material was detected.

According to the present invention, a hydrofluorocarbon can be produced under low pressure in a short period of time at an excellent conversion and a high selectivity. Further, the method of the present invention is a continuous gas phase reaction which requires no special reagent or operation, and therefore it is very advantageous from the industrial point of view. Further, the obtained hydrofluorocarbon can be purified to a product of a higher purity by simple purification treatment.

What is claimed is:

1. A method for producing a hydrofluorocarbon of the formula H$_n$R$_f$H wherein n is 0 or 1, and when n is 0, R$_f$ is a C$_{2-12}$ linear or branched polyfluoroalkyl group, and when n is 1, R$_f$ is a C$_{2-12}$ linear or branched polyfluoroalkylene group, which comprises reacting an iodofluorocarbon of the formula I$_n$R$_f$I wherein n and R$_f$ are as defined above, with hydrogen at a temperature of not higher than 450° C. in a gas phase.

2. The method according to claim 1, wherein the reaction is carried out in the presence of a hydrogenation catalyst.

3. The method according to claim 2, wherein the hydrogenation catalyst is a hydrogenation catalyst containing at least one member selected from the group consisting of alumina, active carbon, zeolite and Group 8 elements.

4. The method according to claim 2, wherein the hydrogenation catalyst is a hydrogenation catalyst containing palladium, palladium and gold, or palladium and silver.

5. The method according to claim 1, wherein n is 0, and R$_f$ is CF$_3$CF$_2$CF$_2$CF$_2$CF$_2$CF$_2$—.

6. The method according to claim 2, wherein n is 0, and R$_f$ is CF$_3$CF$_2$CF$_2$CF$_2$CF$_2$CF$_2$—.

7. The method according to claim 3, wherein n is 0, and R$_f$ is CF$_3$CF$_2$CF$_2$CF$_2$CF$_2$CF$_2$—.

8. The method according to claim 4, wherein n is 0, and R$_f$ is CF$_3$CF$_2$CF$_2$CF$_2$CF$_2$CF$_2$—.

9. The method according to claim 1, wherein n is 1, and R$_f$ is —CF$_2$CF$_2$CF$_2$CF$_2$—.

10. The method according to claim 2, wherein n is 1, and R$_f$ is —CF$_2$CF$_2$CF$_2$CF$_2$—.

11. The method according to claim 3, wherein n is 1, and R$_f$ is —CF$_2$CF$_2$CF$_2$CF$_2$—.

12. The method according to claim 4, wherein n is 1, and R$_f$ is —CF$_2$CF$_2$CF$_2$CF$_2$—.

13. The method according to claim 2, wherein the reaction temperature is from 200° C. to 350° C.

14. The method according to claim 1, wherein the reaction is carried out in the absence of a catalyst.

15. The method according to claim 14, wherein the reaction temperature is from 300° C. to 450° C.

16. The method of claim 1, wherein when n is 0, R$_f$ is a C$_{3-12}$ linear or branched polyfluoroalkyl group and when n is 1, R$_f$ is a C$_{3-12}$ linear or branched polyfluoroalkylene group.

17. The method of claim 1, wherein when n is 0, R$_f$ is a C$_{3-8}$ linear or branched polyfluoroalkyl group and when n is 1, R$_f$ is a C$_{3-8}$ linear or branched polyfluoroalkylene group.

18. The method of claim 1, wherein the reaction temperature is from 150° to 450° C.

* * * * *